(12) United States Patent
Mackenzie

(10) Patent No.: US 9,168,157 B2
(45) Date of Patent: Oct. 27, 2015

(54) SEALING SHEATH FOR PROSTHETIC LINER AND RELATED METHODS

(71) Applicant: OSSUR AMERICAS, INC., Foothill Ranch, CA (US)

(72) Inventor: Maitland Craig Mackenzie, Orlando, FL (US)

(73) Assignee: OSSUR AMERICAS, INC., Foothill Ranch, CA (US)

( * ) Notice: Subject to any disclaimer, the term of this patent is extended or adjusted under 35 U.S.C. 154(b) by 62 days.

(21) Appl. No.: 13/826,748

(22) Filed: Mar. 14, 2013

(65) Prior Publication Data

US 2013/0197670 A1    Aug. 1, 2013

Related U.S. Application Data

(63) Continuation of application No. 13/748,891, filed on Jan. 24, 2013, now Pat. No. 9,072,611, and a continuation of application No. 12/657,468, filed on Jan. 21, 2010, now Pat. No. 8,372,159.

(60) Provisional application No. 61/205,512, filed on Jan. 21, 2009.

(51) Int. Cl.
*A61F 2/50* (2006.01)
*A61F 2/78* (2006.01)
*A61F 2/80* (2006.01)

(52) U.S. Cl.
CPC .............. *A61F 2/5046* (2013.01); *A61F 2/7812* (2013.01); *A61F 2002/7818* (2013.01); *A61F 2002/802* (2013.01); *A61F 2002/805* (2013.01)

(58) Field of Classification Search
CPC ................ A61F 2/5044; A61F 2/5046; A61F 2002/5055–2002/5056; B29C 70/48; B29C 45/14786
See application file for complete search history.

(56) References Cited

U.S. PATENT DOCUMENTS

| 980,457 A | 1/1911 | Toles |
|---|---|---|
| 1,389,824 A | 11/1921 | Abrams |

(Continued)

FOREIGN PATENT DOCUMENTS

| AT | 369978 B | 2/1983 |
|---|---|---|
| DE | 484363 C | 10/1929 |

(Continued)

OTHER PUBLICATIONS

Extended European Search Report from EP Application No. 14161004.8, May 22, 2014, 6 pages.

(Continued)

*Primary Examiner* — Jill Heitbrink
(74) *Attorney, Agent, or Firm* — Workman Nydegger

(57) ABSTRACT

The sealing sheath is for use with a prosthetic socket and associated liner. The sealing sheath includes a textile tube for surrounding at least a portion of a liner that is configured to wear on a residual limb. An annular seal, e.g. an elastomeric or silicone seal, is positioned adjacent a proximal end of the textile tube and continuously extends from an inside of the textile tube configured to be adjacent the liner, through the textile tube to an outside thereof configured to be adjacent an inside of the prosthetic socket. The annular seal may include a first wing on an inside of the textile tube configured to be adjacent the liner, a second wing on an outside of the textile tube configured to be adjacent an inside of the prosthetic socket, and a base connecting lower ends of the first and second wings to define a v-shaped cross-section of the annular seal.

18 Claims, 3 Drawing Sheets

(56) References Cited

U.S. PATENT DOCUMENTS

| | | | |
|---|---|---|---|
| 1,893,853 A | 1/1933 | Tullis | |
| 2,325,656 A | 8/1943 | Brophy | |
| 2,464,443 A | 3/1949 | Ganoe et al. | |
| 2,530,285 A | 11/1950 | Catranis | |
| 2,533,404 A | 12/1950 | Sharp et al. | |
| 2,689,351 A | 10/1951 | Schindler | |
| 2,634,424 A | 4/1953 | O'Gorman et al. | |
| 2,671,225 A | 3/1954 | Schoene et al. | |
| 2,808,593 A | 10/1957 | Andersen | |
| 3,393,407 A | 7/1968 | Andel | |
| 3,587,572 A | 6/1971 | Evans | |
| 3,671,980 A | 6/1972 | Baird | 3/20 |
| 3,947,897 A | 4/1976 | Owens | |
| 4,128,903 A | 12/1978 | Marsh et al. | |
| 4,215,679 A | 8/1980 | Rustin | |
| 4,319,413 A | 3/1982 | Mattil | |
| 4,347,204 A | 8/1982 | Takagi et al. | |
| 4,474,573 A | 10/1984 | Detty | |
| 4,635,626 A | 1/1987 | Lerman | |
| 4,738,249 A | 4/1988 | Linman et al. | |
| 4,767,735 A | 8/1988 | Ewen et al. | |
| 4,885,828 A | 12/1989 | Kozlowski | |
| 4,908,037 A | 3/1990 | Ross | |
| 4,923,474 A | 5/1990 | Klasson et al. | 623/33 |
| 5,007,937 A | 4/1991 | Fishman et al. | 623/34 |
| 5,055,528 A | 10/1991 | Kioka et al. | |
| 5,122,583 A | 6/1992 | Ewen et al. | |
| 5,139,523 A | 8/1992 | Paton et al. | 623/37 |
| 5,163,965 A | 11/1992 | Rasmusson et al. | 623/36 |
| 5,226,918 A | 7/1993 | Silagy et al. | 623/32 |
| 5,244,716 A | 9/1993 | Thornton et al. | |
| 5,314,496 A | 5/1994 | Harris et al. | 623/31 |
| 5,376,129 A | 12/1994 | Raulkner et al. | 623/33 |
| 5,376,131 A | 12/1994 | Lenze et al. | 623/34 |
| 5,387,245 A | 2/1995 | Fay et al. | |
| 5,549,709 A | 8/1996 | Caspers | 623/26 |
| 5,571,208 A | 11/1996 | Caspers | |
| 5,571,209 A | 11/1996 | Brown, Sr. | |
| 5,593,454 A | 1/1997 | Helmy | |
| 5,658,353 A | 8/1997 | Layton | 623/34 |
| 5,702,489 A | 12/1997 | Slemker | 623/34 |
| 5,718,925 A | 2/1998 | Kristinsson et al. | 425/2 |
| 5,728,168 A | 3/1998 | Laghi et al. | |
| 5,728,170 A | 3/1998 | Becker et al. | 623/37 |
| 5,735,906 A | 4/1998 | Caspers | 623/34 |
| 5,830,237 A | 11/1998 | Kania | |
| 5,885,674 A | 3/1999 | Maemoto et al. | |
| 5,888,216 A | 3/1999 | Haberman | 623/36 |
| 5,888,230 A | 3/1999 | Helmy | |
| 5,904,722 A | 5/1999 | Caspers | 623/34 |
| 5,931,872 A | 8/1999 | Lohmann | 623/36 |
| 5,972,036 A | 10/1999 | Kristinsson et al. | 623/33 |
| 5,980,577 A | 11/1999 | Radis et al. | |
| 6,076,284 A | 6/2000 | Terlizzi | |
| 6,136,039 A | 10/2000 | Kristinsson et al. | |
| 6,149,691 A | 11/2000 | Fay et al. | 623/37 |
| 6,171,431 B1 | 1/2001 | Gallagher, Jr. et al. | |
| 6,231,616 B1 | 5/2001 | Helmy | 623/34 |
| 6,231,617 B1 | 5/2001 | Fay | 623/36 |
| 6,273,918 B1 | 8/2001 | Yuhasz et al. | 623/33 |
| 6,287,345 B1 | 9/2001 | Slemker et al. | 623/34 |
| 6,361,568 B1 | 3/2002 | Hoerner | 623/32 |
| 6,368,357 B1 | 4/2002 | Schon et al. | |
| 6,406,499 B1 | 6/2002 | Kania | |
| 6,468,938 B1 | 10/2002 | Govoni et al. | |
| 6,485,776 B2 | 11/2002 | Janusson et al. | |
| 6,508,842 B1 | 1/2003 | Caspers | 623/32 |
| 6,544,292 B1 | 4/2003 | Laghi | |
| 6,554,868 B1 | 4/2003 | Caspers | 623/34 |
| 6,585,774 B2 | 7/2003 | Dean, Jr. et al. | 623/37 |
| 6,626,952 B2 | 9/2003 | Janusson et al. | |
| 6,645,253 B2 | 11/2003 | Caspers | 623/26 |
| 6,706,364 B2 | 3/2004 | Janusson et al. | |
| 6,726,726 B2 | 4/2004 | Caspers | 623/34 |
| 6,761,742 B2 | 7/2004 | Caspers | 623/34 |
| 6,852,269 B2 | 2/2005 | Eberle et al. | |
| 6,926,742 B2 | 8/2005 | Caspers et al. | |
| 6,964,688 B1 | 11/2005 | Kania | |
| 7,001,563 B2 | 2/2006 | Janusson et al. | |
| 7,025,793 B2 | 4/2006 | Egilsson | |
| 7,118,602 B2 | 10/2006 | Bjarnason | |
| 7,144,429 B2 | 12/2006 | Carstens | |
| 7,169,188 B2 | 1/2007 | Carstens | |
| 7,169,189 B2 | 1/2007 | Bjarnason et al. | |
| 7,235,108 B2 | 6/2007 | Carstens | |
| 7,291,182 B1 | 11/2007 | Kania | |
| 7,351,264 B2 | 4/2008 | Wilson | |
| 7,427,297 B2 | 9/2008 | Patterson et al. | |
| 7,592,286 B2 | 9/2009 | Morini et al. | |
| 7,749,281 B2 | 7/2010 | Egilsson | |
| 7,771,487 B2 | 8/2010 | Mantelmacher | |
| 8,034,120 B2 | 10/2011 | Egilsson et al. | |
| 8,097,043 B2 | 1/2012 | Egilsson | |
| 8,372,159 B2 | 2/2013 | Mackenzie | |
| 2001/0005798 A1 | 6/2001 | Caspers | 623/34 |
| 2001/0016781 A1 | 8/2001 | Caspers | 623/34 |
| 2002/0040248 A1 | 4/2002 | Karason | 623/37 |
| 2002/0087215 A1 | 7/2002 | Caspers | 623/34 |
| 2002/0091449 A1 | 7/2002 | Caspers et al. | 623/34 |
| 2002/0099450 A1 | 7/2002 | Dean, Jr. et al. | 623/26 |
| 2002/0165619 A1 | 11/2002 | Hellberg | |
| 2002/0183859 A1 | 12/2002 | Houser | |
| 2003/0181989 A1 | 9/2003 | Eberle et al. | |
| 2003/0191539 A1 | 10/2003 | Caspers | 623/35 |
| 2004/0024322 A1 | 2/2004 | Caspers | |
| 2004/0030411 A1 | 2/2004 | Caspers | 623/37 |
| 2004/0098136 A1 | 5/2004 | Caspers | 623/34 |
| 2004/0122528 A1 | 6/2004 | Egilsson | 623/34 |
| 2004/0143345 A1 | 7/2004 | Caspers | 623/36 |
| 2004/0167638 A1 | 8/2004 | Caspers | 623/27 |
| 2004/0181290 A1 | 9/2004 | Caspers | 623/34 |
| 2004/0236434 A1 | 11/2004 | Carstens | 623/34 |
| 2004/0243251 A1 | 12/2004 | Carstens | 623/34 |
| 2004/0243252 A1 | 12/2004 | Carstens | 623/34 |
| 2005/0101693 A1* | 5/2005 | Arbogast et al. | 523/122 |
| 2005/0216095 A1 | 9/2005 | Egilsson | |
| 2005/0240282 A1 | 10/2005 | Rush et al. | |
| 2005/0240283 A1 | 10/2005 | Kania | |
| 2005/0267598 A1 | 12/2005 | Bjarnason et al. | |
| 2005/0267599 A1 | 12/2005 | Bjarnason | |
| 2006/0212128 A1 | 9/2006 | Nachbar | |
| 2007/0005149 A1 | 1/2007 | Egilsson et al. | |
| 2007/0021295 A1 | 1/2007 | Morini et al. | |
| 2007/0027556 A1 | 2/2007 | Wilson | |
| 2007/0043450 A1 | 2/2007 | Pickering et al. | |
| 2007/0061017 A1 | 3/2007 | Wilson | |
| 2007/0123998 A1 | 5/2007 | Egilsson et al. | |
| 2007/0179606 A1 | 8/2007 | Huyghe et al. | |
| 2008/0147202 A1 | 6/2008 | Danzig et al. | |
| 2008/0188949 A1 | 8/2008 | MacKenzie | |
| 2008/0221705 A1 | 9/2008 | Scussel | |
| 2008/0221706 A1 | 9/2008 | Scussel et al. | |
| 2008/0269914 A1 | 10/2008 | Coppens et al. | |
| 2009/0036999 A1 | 2/2009 | Egilsson et al. | |
| 2009/0069171 A1 | 3/2009 | Sagae | |
| 2009/0157196 A1 | 6/2009 | Danzig et al. | |
| 2009/0182435 A1 | 7/2009 | Haberman | |
| 2009/0198346 A1 | 8/2009 | Perkins et al. | |
| 2009/0240344 A1 | 9/2009 | Colvin et al. | |
| 2009/0306791 A1 | 12/2009 | Slemker et al. | |
| 2010/0070051 A1 | 3/2010 | Carstens | |
| 2010/0185300 A1 | 7/2010 | Mackenzie | |
| 2010/0249950 A1 | 9/2010 | Bielefeld | |
| 2010/0274364 A1 | 10/2010 | Pacanowsky et al. | |
| 2010/0318196 A1 | 12/2010 | Egilsson | |
| 2011/0029096 A1 | 2/2011 | Laghi | |
| 2011/0035027 A1 | 2/2011 | McCarthy | |
| 2011/0054635 A1 | 3/2011 | Watts | |
| 2011/0071649 A1 | 3/2011 | McKinney | |
| 2011/0077748 A1 | 3/2011 | Egilsson et al. | |
| 2011/0118854 A1 | 5/2011 | Halldorsson | |
| 2012/0041568 A1 | 2/2012 | Mackenzie | |

(56) References Cited

U.S. PATENT DOCUMENTS

| | | |
|---|---|---|
| 2013/0053982 A1 | 2/2013 | Halldorsson |
| 2013/0138224 A1 | 5/2013 | Mackenzie |
| 2013/0197670 A1 | 8/2013 | Mackenzie |

FOREIGN PATENT DOCUMENTS

| | | |
|---|---|---|
| DE | 745 981 | 5/1944 |
| DE | 813190 | 9/1951 |
| DE | 1795809 | 9/1959 |
| DE | 2060239 | 6/1972 |
| DE | 2127269 A1 | 12/1972 |
| DE | 2540138 | 3/1977 |
| DE | 2544446 A1 | 4/1977 |
| DE | 3221920 | 4/1983 |
| DE | 3508919 | 11/1989 |
| DE | 9419208 | 11/1994 |
| EP | 0 631 765 | 9/1998 |
| FR | 2420335 A1 | 10/1979 |
| FR | 2539616 A1 | 7/1984 |
| FR | 2 828 093 A1 | 8/2001 |
| GB | 267988 | 9/1925 |
| GB | 263377 | 12/1926 |
| GB | 826041 A | 12/1959 |
| GB | 2069847 | 9/1981 |
| GB | 2087727 | 6/1982 |
| JP | H0623406 A | 2/1994 |
| JP | H07109314 A | 4/1995 |
| JP | 07155343 | 6/1995 |
| JP | H09104714 A | 4/1997 |
| JP | 2637076 B2 | 8/1997 |
| JP | 2740503 B2 | 4/1998 |
| JP | H10182740 B2 | 7/1998 |
| JP | 2001055413 A | 2/2001 |
| JP | 2002500697 A | 1/2002 |
| JP | 2006176565 A | 7/2006 |
| JP | 2006316160 A | 11/2006 |
| JP | 2006528271 A | 12/2006 |
| JP | 3984304 B2 | 10/2007 |
| WO | WO 97/34548 | 9/1997 |
| WO | 00/74611 | 12/2000 |
| WO | 01/54631 | 8/2001 |
| WO | 01/67842 A1 | 9/2001 |
| WO | WO 02/26158 | 4/2002 |
| WO | 03/024367 | 3/2003 |
| WO | 03/024370 | 3/2003 |
| WO | 03/039398 | 5/2003 |
| WO | 03/099173 | 12/2003 |
| WO | 2004060136 A2 | 7/2004 |
| WO | 2010085336 A1 | 7/2010 |
| WO | 2013005735 A1 | 1/2013 |

OTHER PUBLICATIONS

Search Report Regarding, "Silicone-Only Suspension (SOS) with Socket-Loc and the Ring for the Lower Limb", found at http://www.oandp.org/jpo/library/1995_01_002.asp. Journal of Prosthetics and Orthotics 1995; vol. 7, No. 1, p. 2.
International Search Report and Written Opinion Issued in PCT/US2012/051645, Dec. 3, 2012.
Iceross® Confort® Locking/Cushion product information brochure, Mar. 27, 2009, 3 pages.
Iceross® Dermo, product information sheets from Internet, http/www.ossur.com/prosthetics/liners/dermo, Mar. 27, 2009, 2 sheets.
Military inStep: Prosthetic Socks and Liners, product information sheets from Internet, http/www.annputee-coalition.org/military-in-step/prosthetic-socks, Mar. 27, 2009, 3 pages.
Prosthetic & Orthotic Update NewsLetter, No. 32, Internet Search conducted Mar. 27, 2009, 4 pages.
Walopur® Platilon@U, Product Information Brochure of Epurex Films GmbH & Co., KG, Internet Search result conducted Mar. 27, 2009, 2 pages.
Supplementary EP Search Report from EP Application No. 07837275.2, Feb. 19, 2014, 6 pages.
EP 03 78 9861—Supplementary European Search Report.
ESP Opti-Seal, Product Installation Instructions, http://www.wearesp.com, Downloaded Dec. 12, 2014, 1 page.
ESP Opti-Seal, "The Most Versatile Suspension System Availible", www.wearesp.com, Downloaded Dec. 12, 2014, 2 pages.
ESP Secure-Ring System (SRS), http://www.wearesp.com, Downloaded Dec. 12, 2014, 1 page.
ESP Secure-Ring System (SRS), Product Instructions Sheet, http://www.wearesp.com, downloaded Dec. 12, 2014, 2 pages.

* cited by examiner

SEALING SHEATH FOR PROSTHETIC LINER AND RELATED METHODS

FIELD OF THE INVENTION

The present invention relates to the field of prosthetic and orthotic liners and/or sleeves (i.e. skin-socket interface liners and sleeves), and more particularly to custom and production ("off the shelf") prosthetic liners, sleeves, and associated methods.

BACKGROUND OF THE INVENTION

Liners provide a soft, flexible interface between a residual limb of an amputee and a hard socket to which a prosthetic device is secured. Such liners are typically made of an elastomer material such as silicone. Such liners may also be used in connection with orthotic devices. Suspension sleeves are a flexible tube used to secure the prosthetic device to the patients limb. The sleeve may be a sealing sleeve, or a suspension sleeve. Both types start on the prosthetic device and finish on the patients limb. Supportive sleeves can be used in an orthotic device to support a joint or limb of a patient.

Prosthetic suspension liners are described in prior patents, and may be fabricated of elastomer or rubber materials, and are used to cushion a post-operative stump or residual limb with respect to a prosthesis that is installed over the residual limb and coupled to the liner, e.g. by a conventional locking device.

Such liners should conform closely with the residual limb, accommodate all surface contours and sub-surface bone elements of the residual limb, and provide a comfortable cushion between the residual limb and the hard socket of the prosthesis that is to be fitted over the residual limb. Various silicone rubber or elastomer materials are used for suspension liners. Such elastomer materials having an appropriate hardness/softness, elongation, tensile, and other properties, such as bio-inertness (resulting in no skin reaction), have been successfully used for suspension liners.

The elastomer forming the liner or sleeve frictionally engages and remains attached to the skin of a residual limb so that the limb is retained within the prosthetic socket in a comfortable, non-irritating manner. For example, liners may be used for any level of amputation both upper and lower limb.

When an amputee walks air inside the socket allows the socket to fall away from the amputee during swing phase (the time the prosthesis is in the air between steps) causing an accelerated impact of the residual limb and the bottom of the socket when the heel hits the floor. By removing the air in the socket the prosthesis is held closer to the residual limb during swing phase reducing the accelerated impact at heel strike. There are various ways to seal the proximal portion of the socket and the liner that covers the amputee's residual limb. The most common is the use of a sealing sleeve. The sealing sleeve is attached to the outside of the socket and extends up onto the amputee's limb usually sealing on the liner.

Problems with sealing sleeves include, but are not limited to, punctures, bunching behind the knee, restricted knee flexion, and tearing along the brim of the socket.

U.S. Pat. No. 7,025,793 to Egilsson is directed to a seal but it is attached directly to the liner, which does not allow for optimal placement of the seal. The design configuration may not allow for higher vacuum sockets. Another existing seal is disclosed in U.S. Pat. No. 7,144,429 to Carstens. The seal arrangement includes a cuff-like base with a sealing lip on an outside thereof. The lip has two flaps to seal on both the liner and inner socket wall but nothing to hold the base in place, which may allow for the possibility of migration of the seal proximally during donning of the liner, compromising the seal.

SUMMARY OF THE INVENTION

It is an object of the present invention to provide a more reliable seal for use with prosthetic sockets and associated liners.

This and other objects, advantages and features in accordance with the present invention are provided by a sealing sheath for use with a prosthetic socket and associated liner, the sealing sheath including a textile tube for surrounding at least a portion of a liner that is configured to wear on a residual limb. An annular seal, e.g. an elastomeric or silicone seal, is positioned adjacent a proximal end of the textile tube and continuously extends from an inside of the textile tube configured to be adjacent the liner, through the textile tube to an outside thereof configured to be adjacent an inside of the prosthetic socket.

The textile tube may include a closed distal end opposite the proximal end which is open. The textile tube may define a wicking layer for distributing vacuum within an area defined between the liner and the prosthetic socket and sealed by the annular seal.

The annular seal may comprise a first wing on an inside of the textile tube configured to be adjacent the liner, a second wing on an outside of the textile tube configured to be adjacent an inside of the prosthetic socket, and a base connecting lower ends of the first and second wings to define a v-shaped cross-section of the annular seal. The first wing may extend through the textile tube from the inside to the outside thereof. The base may extend through the textile tube from the inside to the outside thereof. The second wing may have a tapered width from the lower end to an upper end thereof.

Objects, advantages and features in accordance with the present invention are also provided by a method of making a sealing sheath for use with a prosthetic socket and associated liner, the method including providing a textile tube for surrounding at least a portion of a liner that is configured to wear on a residual limb, and forming an annular seal adjacent a proximal end of the textile tube and continuously extending from an inside of the textile tube configured to be adjacent the liner, through the textile tube to an outside thereof configured to be adjacent an inside of the prosthetic socket.

Forming the annular seal may comprise forming a first wing on an inside of the textile tube configured to be adjacent the liner, a second wing on an outside of the textile tube configured to be adjacent an inside of the prosthetic socket, and a base connecting lower ends of the first and second wings to define a v-shaped cross-section of the annular seal. The second wing may be formed with a tapered width from the lower end to an upper end thereof. Also, forming the annular seal may include the use of a mold having a body for holding the textile tube, and body portions corresponding to a shape of the annular seal. As such, forming the annular seal may further comprise providing silicone in the mold to fill the body portions and define the annular seal.

DETAILED DESCRIPTION OF THE PREFERRED EMBODIMENTS

Figure 1:
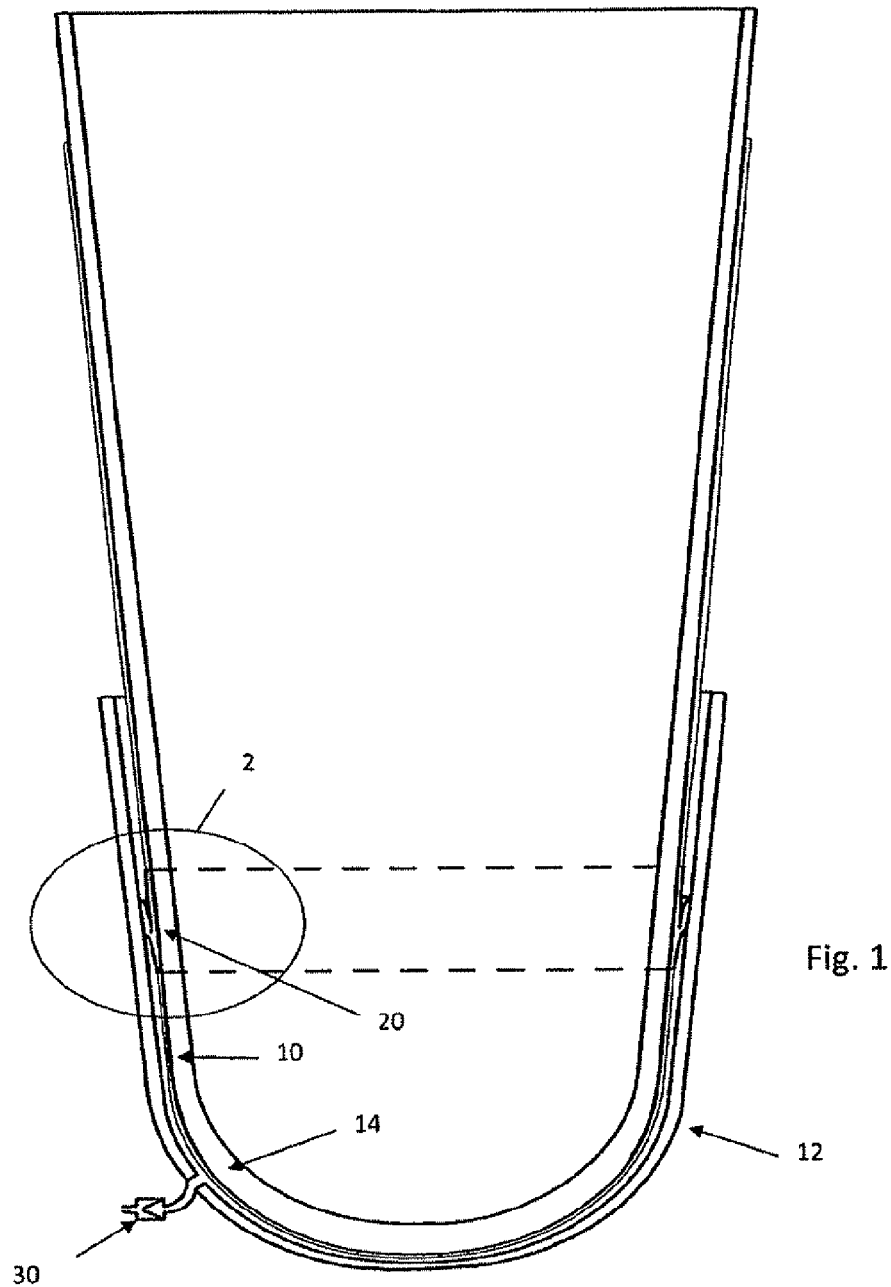
FIG. 1 is a cross-sectional view of a vacuum socket and liner, and a sealing sheath and seal in accordance with features of the present invention.

The present invention will now be described more fully hereinafter with reference to the accompanying drawings in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout and prime notations are used in alternate embodiments.

The following description refers to, by example, a liner associated with the knee, however, the features of the invention apply to liners and sleeves for use with any limb/joint area that may benefit from the use of a sealing sheath as described herein. Features of the present invention are directed to a sealing sheath for a prosthetic or orthotic liner or sleeve and associated methods of making and using. Dimensions of layers in the drawings may be exaggerated for ease of explanation.

Figure 2:
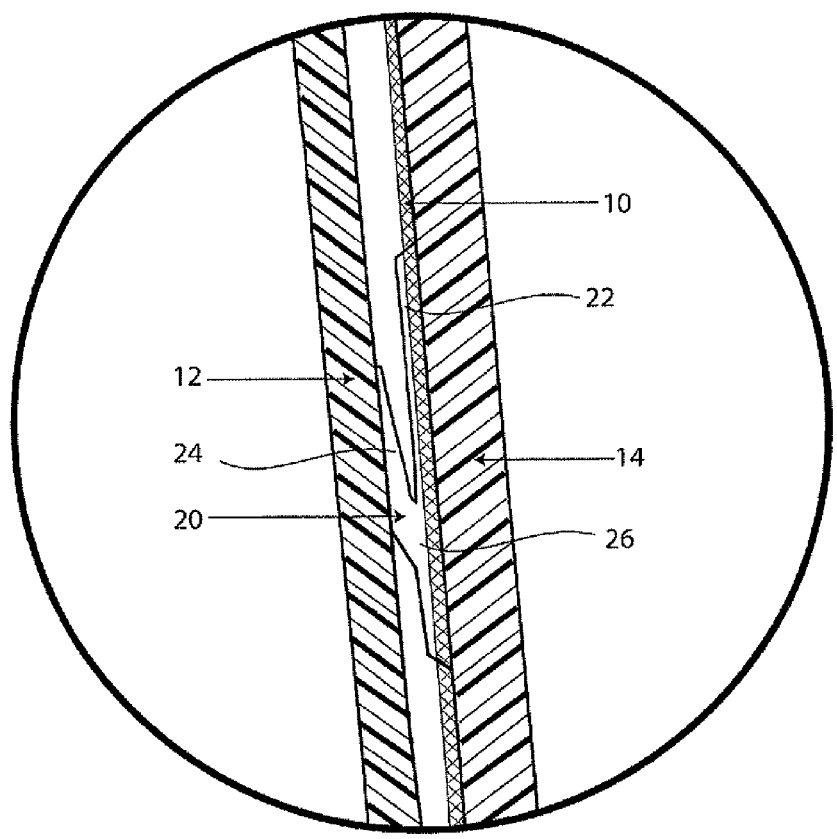
FIG. 2 is an enlarged view illustrating details of the sealing sheath and seal of FIG. 1 between the socket wall and liner.

Referring to FIGS. 1-2 below, the approach of the present invention will be described. As discussed above, a conventional sealing sleeve is normally worn on the outside of the socket and seals on the portion of the liner that extends out of the top of the socket. This approach leaves the sleeve exposed to the outside environment, and such exposure is the source of many of the problems associated with sleeves such as punctures, bunching behind the knee, restricted knee flexion, and tearing along the brim of the socket.

The sealing sheath 10 of the present invention is positioned on the inside of a socket 12 protecting it from the outside environment, and it is placed on a liner 14 at a position, e.g. chosen by the prosthetist by sealing, sewing or otherwise attaching the sheath 10 or textile or fabric tube at a specific distance from the bottom of the uncovered liner 14, to provide a sufficient sealing area or optimize the sealing area.

A first wing 22 of the v-shaped annular seal 20 is against the uncovered liner 14 and a second wing 24 is positioned against the inner socket wall 12. As a one-way expulsion valve 30 in the distal portion of the socket 12 (or any other evacuation approach) evacuates air, by either mechanical or electrical means, a vacuum is created beneath the level of the seal 20. The sheath 10 or fabric tube holds the seal 20 in the proper position on the uncovered liner 14 as the amputee inserts the limb into the socket 12. The higher the force of the vacuum the more securely the wings 22/24 of the seal are held against the liner 14 and inner socket wall 12.

Since the seal 20 is preferably positioned below the joint, e.g. knee, joint flexion is not inhibited and the there is no extra material around the joint to cause any bunching. Punctures and tearing are also reduced or eliminated because the seal is inside the socket, and the tearing that occurs from movement at the knee may also be reduced or eliminated.

As illustrated in the enlarged view of FIG. 2, the annular seal 20 may include a first wing 22 on an inside of the textile tube 10 configured to be adjacent an outer surface of the liner 14. A second wing 24 is on an outside of the textile tube 10 configured to be adjacent an inside surface of the prosthetic socket 12. A base 26 connects lower ends of the first 22 and second 24 wings to define a v-shaped cross-section of the annular seal 20. The first wing 22 may extend through the textile tube 10 from the inside to the outside thereof. The base 26 may extend through the textile tube 10 from the inside to the outside thereof. The first 22 and second 24 wings may have a tapered width from the lower end to an upper end thereof. Such a tapered seal design, i.e. from bottom to top making the upper edge thinner than the base 26, gives the seal 20 more flexibility, allowing the seal more mobility to allow for any forces during ambulation that would try to pull the seal away from both the liner 14 and inner socket wall 12. In the present invention, when vacuum is applied to the underside of the seal 20, the vacuum draws the wings 22/24 of the seal 20 tighter against the socket 12 and liner 14.

The seal 20 is connected, e.g. during molding or curing, to the sheath 10 or fabric tube that is separate from the liner 14. This arrangement allows for the sealing sheath 10 to be replaced, e.g. if damaged, at a lower cost than that of replacing an entire liner 14. Of course, if desired, the sheath 10 or portions thereof could be attached to the liner.

The seal 20 is preferably made of silicone or any other elastomer that provides an adequate seal, and protrudes, extends through or is otherwise formed on both sides of the sheath 10 or fabric tube to allow for a complete seal against the liner 14.

Figure 3:
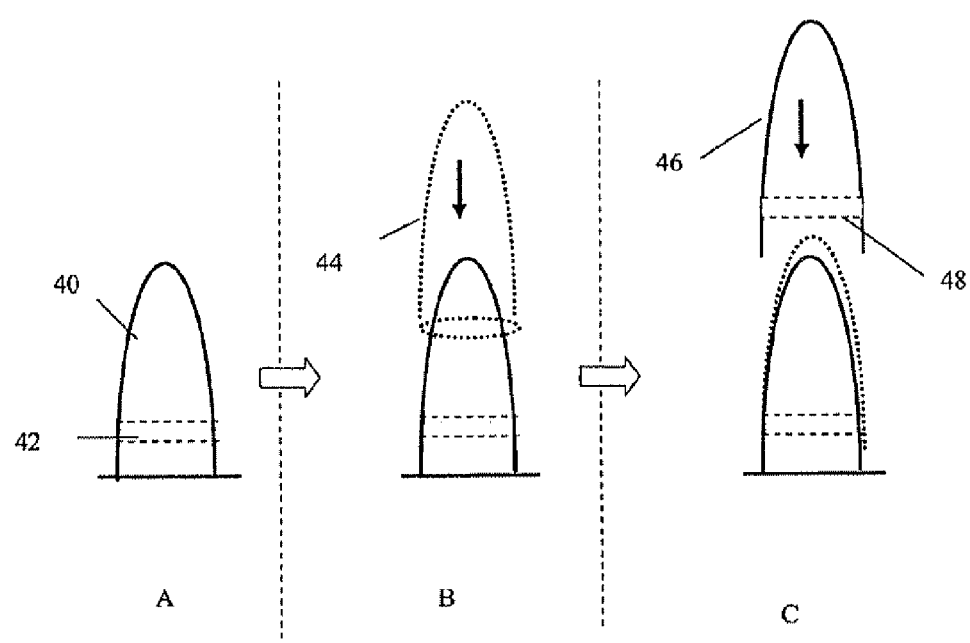
FIG. 3 is a schematic diagram illustrating various steps in an embodiment of a method for making the sealing sheath of FIG. 1.

With reference to FIG. 3, the sealing sheath 10 may be made using a male 40 and female 46 mold. The male mold 40 is a cylinder with a small annular indent 42 corresponding to the portion of the seal 20 on the inner portion of the sealing sheath 10 (step A). A section of fabric 44 is pulled over the male mold 40 (step B). The female mold 46, e.g. having an annular indent 48 corresponding to the shape of the seal 20, is then placed over the male mold 40 and fabric 44 with indexing on the male mold so the main shape of the seal lines up with the indent 48 in the male mold 40 (step C). The combination of molds are then injected with the appropriate silicone. The fabric 44 will bridge the small annular indent 42 in the male mold 40 allowing for the silicone to pass through the fabric and ensuring a silicone layer on both sides of the fabric.

The sheath material 10 or fabric tube may also act as a vacuum wick below the seal 20 ensuring that the seal is held against the socket 12 and liner 14 tightly. Such a fabric tube 10 can also be sewn and trimmed to accommodate any residual limb length. By sewing the fabric tube 10, the clinician or amputee can place the seal at a preferable height on the liner 14 from the distal end thereof. The fabric tube 10 also stops the seal 20 from migrating proximally, or out the top of the socket 12. As discussed above, such migration could cause a loss in vacuum.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

The invention claimed is:

1. A method for making a prosthetic device, comprising the steps of:
   providing a fabric material;
   providing male and female molds;
   placing a section of the fabric material over the male mold;
   placing the female mold having an annular indent corresponding to a shape of a seal over the male mold and fabric material at a localized area along the fabric material between top and bottom portions of the fabric material;

injecting an elastomeric material between the male and female molds at the localized area so as to allow for the elastomeric material to pass through and bridge the fabric to ensure the elastomeric material on both sides of the fabric material at least at the female mold annular indent such that fabric material without the elastomeric material border above and below the localized area.

2. The method of claim 1, wherein the male mold includes an annular indent.

3. The method of claim 2, further comprising the step of indexing the male mold annular indent to the female mold annular indent.

4. The method of claim 3, further comprising the step of injecting the elastomeric material between the annular indents among the male and female molds.

5. The method of claim 1, wherein the male mold is a cylinder having a closed end.

6. The method of claim 5, wherein the female mold is a cylinder corresponding in shape to the male mold.

7. The method of claim 1, wherein the fabric material is configured as a closed-ended tube and defines a wicking layer.

8. The method of claim 1, wherein the elastomeric material is silicone.

9. The method of claim 1, wherein the female mold annular indent defines cavities for forming first and second wings combining to form a v-shaped cross-section and extending outwardly from an outside surface of the fabric material.

10. The method of claim 9, wherein the first wing extends upwardly beyond an upper end of the second wing.

11. The method of claim 10, wherein the cavity for the second wing has a tapered width from a lower end to an upper end thereof.

12. A method for making a prosthetic device, comprising the steps of:
   providing a fabric material defining a wicking layer;
   providing male and female molds, the male mold having an annular indent;
   placing a section of the fabric material over the male mold;
   placing the female mold having an annular indent corresponding to a shape of a seal over the male mold and fabric material;
   indexing the male mold annular indent to the female mold annular indent;
   injecting an elastomeric material between the male and female molds so as to allow for the elastomeric material to pass through and bridge the fabric to ensure the elastomeric material on both sides of the fabric material only at the female and male mold annular indents;
   forming an elastomeric annular seal from the injected elastomeric material only at the female mold annular indent and protruding from an outside surface of the fabric material adjacent the female mold and continuously extending from and along an inside surface of the fabric material adjacent to the male mold.

13. The method of claim 12, wherein the male mold is a cylinder having a closed end and the fabric material is formed as a closed-ended tube adapted in shape to cover the male mold.

14. The method of claim 13, wherein the female mold is a cylinder corresponding in shape to the male mold.

15. The method of claim 12, wherein the elastomeric material is silicone.

16. A method for making a prosthetic device, comprising the steps of:
   providing a fabric material;
   providing male and female molds;
   placing a section of the fabric material over the male mold;
   placing the female mold having an annular indent corresponding to a shape of a seal over the male mold and fabric material;
   injecting an elastomeric material between the male and female molds so as to allow for the elastomeric material to pass through and bridge the fabric to ensure the elastomeric material on both sides of the fabric material at least at the female mold annular indent;
   wherein the female mold annular indent defines cavities for forming first and second wings combining to form a v-shaped cross-section and extending outwardly from an outside surface of the fabric material.

17. The method of claim 16, wherein the first wing extends upwardly beyond an upper end of the second wing.

18. The method of claim 17, wherein the cavity for the second wing has a tapered width from a lower end to an upper end thereof.

* * * * *